US010633310B2

United States Patent
Du et al.

(10) Patent No.: US 10,633,310 B2
(45) Date of Patent: Apr. 28, 2020

(54) PROCESS FOR THE MANUFACTURE OF 2,2-DICHLORO-1,1,1-TRIFLUOROETHANE (HCFC-123) AND/OR HCFC-122 (1,1,2-TRICHLORO-2,2-DIFLUOROETHANE)

(71) Applicant: FUJIAN YONGJING TECHNOLOGY CO., LTD, Fujian (CN)

(72) Inventors: Hongjun Du, Fujian (CN); Wenting Wu, Fujian (CN)

(73) Assignee: FUJIAN YONGJING TECHNOLOGY CO., LTD, Fujian (CN)

( * ) Notice: Subject to any disclaimer, the term of this patent is extended or adjusted under 35 U.S.C. 154(b) by 0 days.

(21) Appl. No.: 16/525,554

(22) Filed: Jul. 29, 2019

(65) Prior Publication Data
US 2020/0031743 A1 Jan. 30, 2020

(30) Foreign Application Priority Data

Jul. 30, 2018 (DE) .................. 10 2018 118 406

(51) Int. Cl.
*C07C 17/20* (2006.01)
*C07C 19/10* (2006.01)
(Continued)

(52) U.S. Cl.
CPC .......... *C07C 17/206* (2013.01); *C07C 17/087* (2013.01); *C07C 19/10* (2013.01); *C07C 19/12* (2013.01)

(58) Field of Classification Search
CPC ....... C07C 17/206; C07C 19/10; C07C 19/12; C07C 17/087
See application file for complete search history.

(56) References Cited

FOREIGN PATENT DOCUMENTS

| CN | 103102241 | 5/2013 |
| CN | 105237334 | 1/2016 |

(Continued)

*Primary Examiner* — Jafar F Parsa
(74) *Attorney, Agent, or Firm* — JCIP Global Inc.

(57) ABSTRACT

The invention pertains to a method in which the production of HCFC-123 (2,2-dichloro-1,1,1-trifluoroethane) and/or of HCFC-122 (1,1,2-trichloro-2,2-difluoroethane) in at least one reaction step takes place in a microreactor. Particularly, in preferred embodiments of the invention pertains to a method in which the production of HCFC-123 (2,2-dichloro-1,1,1-trifluoroethane) and/or of HCFC-122 (1,1,2-trichloro-2,2-difluoroethane) in at least one reaction step takes place in a microreactor that comprises or is made of SiC ("SiC-microreactor"), or in a microreactor that comprises or is made of an alloy, e.g. such as Hastelloy C. In an ebodiment, the processes for the manufacture of HCFC-123 (2,2-dichloro-1,1,1-trifluoroethane) and/or of HCFC-122 (1,1,2-trichloro-2,2-difluoroethane) can be efficiently combined in that HCFC-122 (1,1,2-trichloro-2,2-difluoroethane) produced by the method according the invention by using a microreactor, preferably an SiC-microreactor, may preferably advantageously serve as starting material/and/or intermediate material in the manufacture of HCFC-123 (2,2-dichloro-1,1,1-trifluoroethane), preferably also in a microreactor.

19 Claims, 1 Drawing Sheet

(51) Int. Cl.
*C07C 19/12* (2006.01)
*C07C 17/087* (2006.01)

(56) References Cited

FOREIGN PATENT DOCUMENTS

| | | | |
|---|---|---|---|
| DE | 4005944 | 8/1991 | |
| EP | 0414370 A1 * | 2/1991 | ............. C07C 19/08 |
| EP | 0451746 | 10/1991 | |
| EP | 0781745 | 7/1997 | |
| EP | 1637271 | 5/2011 | |
| WO | 0076945 | 12/2000 | |
| WO | 2016079122 | 5/2016 | |

* cited by examiner

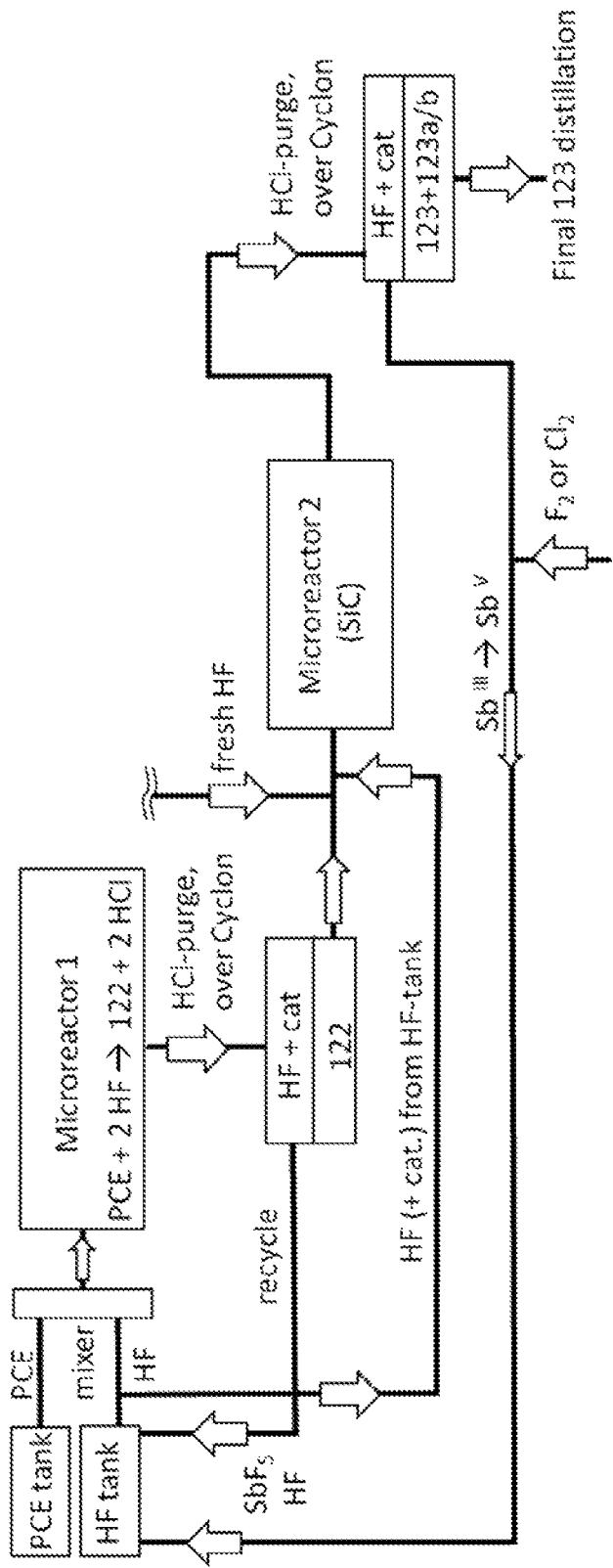

PROCESS FOR THE MANUFACTURE OF 2,2-DICHLORO-1,1,1-TRIFLUOROETHANE (HCFC-123) AND/OR HCFC-122 (1,1,2-TRICHLORO-2,2-DIFLUOROETHANE)

CROSS-REFERENCE TO RELATED APPLICATION

This application claims the priority benefit of Germany application serial no. 10 2018 118 406.9, filed on Jul. 30, 2018. The entirety of the above-mentioned patent application is hereby incorporated by reference herein and made a part of this specification.

BACKGROUND

1. Field of the Invention

The invention relates to a process for the manufacture of HCFC-123 (2,2-dichloro-1,1,1-trifluoroethane) and/or for the manufacture of HCFC-122 (1,1,2-trichloro-2,2-difluoroethane). Especially, the invention relates to a process for the manufacture of HCFC-123 (2,2-dichloro-1,1,1-trifluoroethane), in particular by reacting HCFC-122 (1,1,2-trichloro-2,2-difluoroethane) as a starting material or intermediate material with HF in the presence of the catalyst.

2. Description of Related Art

Processes for the manufacture of HCFC-122 (1,1,2-trichloro-2,2-difluoroethane) and of HCFC-123 (2,2-dichloro-1,1,1-trifluoroethane) are already known in the prior art, as shown by the following representative methods.

For example, a number of one-step production methods are known in conventional batch or continuously operated reactors from the European patent applications EP 781745 A2 (Braun, Palsherm et al.), EP 451746 A2 (Eicher et al.), and the International patent application WO 2016/079122 A1 (Braun et al.). These methods are reacting tetrachloroethylene (perchloroethylene; $Cl_2C=CCl_2$) as a starting material with a Lewis acid to obtain HCFC-122 (1,1,2-trichloro-2,2-difluoroethane) as disclosed in EP 781745 A2; or these methods are reacting tetrachloroethylene (perchlorethylene; $Cl_2C=CCl_2$) as a starting material with a Lewis acid in the presence of HF to obtain HCFC-123 (2,2-dichloro-1,1,1-trifluoroethane) as disclosed in EP 451746 A2 or in WO 2016/079122 A1.

Herein, the EP781745 A2 discloses a catalytic mixture based on partially fluorinated titane and zinc halogenides and their application in the preparation of fluorinated organic compounds, and a liquid phase process for the preparation of organic compounds (I) with ≥1 fluorine (F) atom comprises (a) addition of hydrogen fluoride (HF) to an unsaturated carbon-carbon (C—C) group or (b) chlorine-fluorine (Cl—F) exchange with HF on completely halogenated C atom(s) in the starting material. Both reactions are catalyzed by metal halide, comprising a (partly) fluorinated mixture of titanium (Ti) chloride or bromide in combination with (partly) fluorinated tin tetrachloride ($SnCl_4$) or tetrabromide ($SnBr_4$), in which the Ti:Sn atomic ratio is 9:1 to 1:9. Also claimed is a (partly) fluorinated mixture (II) of Ti tetrachloride ($TiCl_4$) and $SnCl_4$ with a Ti:Sn atomic ratio of 1:9 to 9:1, preferably 1:2 to 2:1, obtained by reacting $TiCl_4$ and $SnCl_4$ with HF, using a molar ratio of HF:($TiCl_4$+$SnCl_4$) of ≥4:1, especially ≥8:1.

Herein, the EP 451746 A2 discloses a method for the production of fluorine containing ethane derivatives, i.e. the preparation of fluorine-containing ethane derivatives, using a catalyst mixture comprising a metal halide and a sulphonic acid derivative, is described. The process is particularly suitable for the preparation of ethane derivatives containing a $CF_3$ group, for example $CF_3CHCl_2$ (HCFC-123) from tetrachloroethylene (perchloroethylene) and for the preparation of $CF_3CHCl_2$ (HFC-134a) from trifluoroethylene.

Herein, the International patent application WO 2016/079122 A1 (Braun et al.) discloses a method for the manufacture of chemical compounds, e.g. of HCFC-123 (2,2-dichloro-1,1,1-trifluoroethane), wherein corrosive and/or abrasive starting compounds, catalysts, intermediates or target compounds; and a suitable reactor are involved. The method is performed in a reactor at least partially made from or at least partially coated with material which is resistant to the reaction mixture, but has a low heat transfer coefficient, and where heat is supplied by a heat exchanger from a material which has a high heat transfer coefficient and high resistance to corrosion and/or abrasion. Preferably, the reactor is coated or at least partially coated with a (chloro)fluoro-substituted material, e.g. PTFE, and the heat exchanger is preferably constructed from silicon carbide. For example, hydrochlorofluorocarbons can be manufactured using HF as a starting compound, and antimony halides as catalyst.

Another, recent one-step production method is knownCN 105237334 A (Faming ZhuanliShenqing, 2016), and relates to a method for combined production of 1,1,2-trifluorotrichloroethane (CFC-113, $CClF_2CFCl_2$) and 1,1,1-trifluorodichloroethane (HCFC-123; $CF_3CHCl_2$). Especially disclosed is a method that comprises the following steps: adding reaction raw materials comprising hydrofluoric acid, hexachloroethane and tetrachloroethylene into a reaction autoclave according to a molar ratio of (10-40):(0.8-2.5):(1.2-3.6), reacting, adding a catalyst for catalysis, reacting at 30-250° C. under 0.3-3.0 Mpa for 2-12 h, washing with water, washing with an alkali, and carrying out rectifying purification to obtain the products 1,1,2-trifluorotrichloroethane and 1,1,1-trifluorodichloroethane, wherein the catalyst can be metal fluoride or metal chloride, the metal fluoride comprises $AlF_3$, $SbF_3$, $SbF_5$ and $ZnF_2$, and the metal chloride comprises $SbCl_5$. The synthetic method claims the advantages of abundant sources and low price of the raw materials, high reaction yield, easy reaction feeding, easy separation and extraction of the generated products, and realization of industrial continuous production.

Furthermore, the following two-step production methods for HCFC-133a ($CF_3CH_2Cl$, the most important intermediate in production of HFC-134a; $CF_3$—$CH_2F$) are known in conventional batch or continuous reactors from the International patent application WO 2000/076945 A2 (Braun et al.), and the Chinese patent application CN 103102241 A (Yang Huimin).

Herein, the WO 2000/076945 A2 discloses a method of UV-activated chlorination, whereby alkanes containing chlorine can be produced by attaching chlorine to C—C-double bonds or C—C-triple bonds or by exchanging hydrogen for chlorine, by bringing the starting compound in the gas or liquid phase into contact with elementary chlorine and irradiating them with UV light with a wavelength of lambda >280 nm. In this way, pentachloroethane ($CCl_3CHCl_2$) can be produced from trichloroethylene ($Cl_2C=CHCl$), CFC-113, from HCFC-123 or HFC-133a, CFC-112a from HCFC-142b or HCFC-123 from HFC-133a. The method is also suitable for purifying HFC-365mfc (1,1,1,3,3-pentafluorobutane) with the aim of separating impurities that can be photochlorinated. The claimed advantages of the method are high yields and excellent selectivity. A reaction scheme for the manufacture of, for example, is as follows:

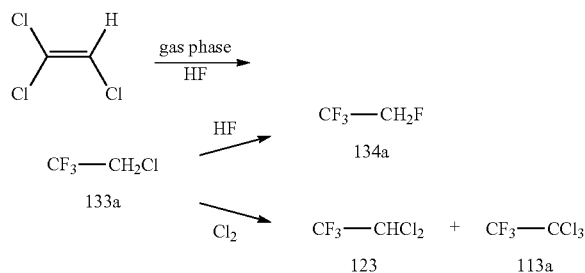

Herein, the CN 103102241 A discloses a process for producing 1,1,1,2-tetrafluoroethane HFC-134a; CF3CH2F) by gas-liquid phase method. The method is taking trichloroethylene and hydrogen fluoride as raw materials, and comprises the following steps of: generating HCFC-133a (1,1,1,2-trifluorochloroethane; $CF_3CH_2Cl$), hydrogen chloride, HCFC-123 and HCFC-131 (1,1,2-trichloro-2-fluoroethane) under the effect of a fluorinating catalyst of trichloroethylene and hydrogen fluoride; performing reaction between potassium hydroxide liquor and hydrogen fluoride to generate potassium fluoride, and performing reaction between potassium fluoride and CFC-133a in the presence of the fluorinating catalyst to generate the product 1,1,1,2-tetrafluoroethane, wherein the temperature is controlled at 250-280° C., and the reaction conversion rate reaches 80%. Hydrogen fluoride and hydrogen chloride generated in the reaction process are less in corrosion to the device, the corrosion to reaction by potassium fluoride is far less than that of hydrogen fluoride, and the investment on the device is less.

The current state of the art has a number of disadvantages. Corrosion problems are not solved in the processes of EP 781745 A2 and of EP 451746 A2. In the processes of WO 2016/079122 A1 and of CN 105237334 A, very large volumes are necessary, i.e. the heat transfer is not effectively provided, and there is possibly high risk potential because of the large amounts of HF involved in the processes. Although, the process disclosed in WO2000/076945 A2, starting from trichloroethylene ($Cl_2C=CHCl$) and yielding HCFC-133a (1,1,1,2-trifluorochloroethane; $CF_3CH_2Cl$) as an intermediate, is industrially feasible, there is no selectivity to yield HCFC-123, but especially coproduction of 113a up to 50% is observed, and the HCFC-122 is not produced or is not producible by the method at all. Like the process of WO2000/076945 A2, also the process of CN 105237334 A starts from trichloroethylene ($Cl_2C=CHCl$) and also provides HCFC-133a (1,1,1,2-trifluorochloroethane; $CF_3CH_2Cl$) as an intermediate that would need to be chlorinated to obtain HCFC-123.

None of the known methods referenced herein before provides HCFC-123 (2,2-dichloro-1,1,1-trifluoroethane) and/or optionally HCFC-122 (1,1,2-trichloro-2,2-difluoroethane) in industrial yields. Also, the known methods are not resources and energy saving because of their poor selectivity and high energy consumption by the required purification by distillation.

SUMMARY

Therefore, it is an object of the present invention to provide a process for the manufacture of HCFC-123 (2,2-dichloro-1,1,1-trifluoroethane) and/or for the manufacture of HCFC-122 (1,1,2-trichloro-2,2-difluoroethane) that industrially feasible, e.g. easily scalable to industrial yields of HCFC-123 and/or optionally of HCFC-122, and which process in particular shows improved (e.g. good) selectivity and low energy consumption for the targeted products of HCFC-123 and/or optionally of HCFC-122. Especially, it is an object of the presentinvention to provide such an improved and/or optimized carbon and energy efficient process for the manufacture of HCFC-123, in particular by reacting HCFC-122 as a starting material or intermediate material with HF in the presence of the catalyst. In particular, it is also an object of the presentinvention to provide such an improved and/or optimized process for the manufacture of HCFC-123 and/or for the manufacture of HCFC-122 wherein the HCFC-123 and/or the HCFC-122 can be easily, e.g. by a method with only low energy consumption, purified and/or isolated, and wherein preferably the process for purifying and/or isolating does not require a distillation.

The objects of the invention are solved as defined in the claims, and described herein after in detail. In particular, the present invention employs in preferred embodiments one or more microreactors in the concerned processes of the invention, i.e. in a process for the manufacture of HCFC-123 (2,2-dichloro-1,1,1-trifluoroethane) or in a process for the manufacture of HCFC-122 (1,1,2-trichloro-2,2-difluoroethane), respectively, and/or, one or more phase separation methodsare employed in preferred embodiments of the present invention.

The German patent application DE 4005944 A1 describes a preparation of 1,1,1-trifluoro-2,2-dichloroethane by liquid phase hydrofluorination, especially of perchloroethylene, in presence of addition products of antimony pentahalide and hydrogen fluoride, wherein a two-phase formation is mentioned. However, the difference to the present invention is that in DE 4005944 A1 solely the volatile products are expelled from the reactor, whereas in the present invention, there is a mixture including catalyst in the phases.

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤4 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. <1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly and/or a larger volume reactor used. Production rates can vary from milliliters per minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor, a pump propels one reagent, which causes a reactant to be sucked in. Also to be mentioned are plug flow reactors and tubular flow reactors.

In one embodiment of the present invention, it is particularly preferred to employ a microreactor.

In an alternative embodiment of the invention, it is also optionally desired to employ another continuous flow reactor than a microreactor, preferably if, for example, the (halogenation promoting, e.g., the halogenation or preferably the halogenation) catalyst composition used in the halogenation, preferably fluorination, tends to get viscous during reaction or is viscous already as a catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤4 mm. In such an embodiment of the invention, it is particularly preferred to employ a continuous flow reactor, a plug flow reactor and/or a tubular flow reactor, with the lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, from about ≥1 up to about ≤6 times higher, from about ≥1 up to about ≤5 times higher, from about ≥1 up to about ≤4 times higher, from about ≥1 up to about ≤3 times higher, or from about ≥1 up to about ≤2 times higher, each as compared to the typical flow rates indicated herein for a microreactor. Preferably, the continuous flow reactor, more preferably the the plug flow reactor and/or a tubular flow reactor, employed in this embodiment of the invention is configured with the construction materials as defined herein for the microreactors. For example, such construction materials are siliconcarbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before lateral dimensions, that for separating simply phase separation methods can be employed, and the non-consumed reaction components may be recycled into the process, or otherwise be used as a product itself, as applicable or desired.

In addition to the preferred embodiments of the present invention using a microreactor in steps (d) and (e), as defined herein and in the claims, in the processes for the manufacture of HCFC-122 (1,1,2-trichloro-2,2-difluoroethane) according to the invention, or in the manufacture of HCFC-123 (2,2-dichloro-1,1,1-trifluoroethane) according to the invention, respectively, in addition or alternatively to using a microreactor, it is also possible to use in steps (d) and (e) to employ a plug flow reactor or a tubular flow reactor, respectively.

Plug flow reactor or tubular flow reactor, and their respective operation conditions are well known to those skilled in the field.

Accordingly, one embodiment relates to a process for the manufacture of HCFC-122 (1,1,2-trichloro-2,2-difluoroethane) or the manufacture of HCFC-123 (2,2-dichloro-1,1,1-trifluoroethane) according to the invention, respectively. The process defined herein and in the claims further comprise steps (d) and (e) described below, in addition to the steps (a) to (c) and (f).

(d) feeding the mixture obtained in (c) into at least one microreactor, into at least one plug flow reactor, and/or into at least one tubular flow reactor, preferably into at least one continuous flow reactor with upper lateral dimensions of about ≤4 mm, more preferably into at least one microreactor, and therein carrying out the reaction of HCFC-122 with HF in the presence of the catalyst (halogenation, preferably fluorination catalyst) to obtain a reaction mixture comprising HCFC-123;

preferably into at least one microreactor under one or more of the following conditions:

flow rate: from about 10 ml/h up to about 400 l/h;
temperature: from about 30° C. up to about 150° C.;
pressure: from about 5 bar up to about 50 bar;
residence time: from about 1 minute up to about 60 minutes;

(e) withdrawing the reaction mixture obtained in (d) from the microreactor(s), from the plug flow reactor(s), and/or from the tubular flow reactor(s), preferably the continuous flow reactor(s) with upper lateral dimensions of about ≤4 mm, more preferably, more preferably from the microreactor(s), to yield a HCFC-123 comprising product, preferably a HCFC-123 product, more preferably a product comprising or consisting essentially of HCFC-123.

Although the use of a continuous flow reactor with upper lateral dimensions of about ≤4 mm, and in particular of a microreactor, is particularly preferred in the present invention, depending on the circumstances, it could be imagined that somebody dispenses with a microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

BRIEF DESCRIPTION OF THE DRAWINGS

FIG. 1 is an exemplary embodiment of a process scheme for the manufacture of HCFC-123 (2,2-dichloro-1,1,1-trifluoroethane) and/or of HCFC-122 (1,1,2-trichloro-2,2-difluoroethane).

DESCRIPTION OF THE EMBODIMENTS

In the following, the invention is more particularly described in the context of using a microreactor. Preferentially, a microreactor used according to the invention is a ceramic continuous flow reactor, more preferably aSiC (silicon carbide) continuous flow reactor, and can be used for material production at a multi-scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400 l/h); intensified chemical production where space is limited; unrivaledchemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, contains silicon and carbon, and is well known to those skilled in the art. For example, synthetic SiC powder has been mass-produced and processed for many technical applications.

For example, in the embodiments of the invention, the objects are achieved by a method in which the production of HCFC-123 (2,2-dichloro-1,1,1-trifluoroethane) and/or of HCFC-122 (1,1,2-trichloro-2,2-difluoroethane) in at least one reaction step takes place in a microreactor. Particularly, in preferred embodiments of the invention the objects are achieved by a method in which the production of HCFC-123 (2,2-dichloro-1,1,1-trifluoroethane) and/or of HCFC-122 (1,1,2-trichloro-2,2-difluoroethane) in at least one reaction step takes place in a microreactor that comprises or is made of SiC ("SiC-microreactor"), or in a microreactor that comprises or is made of an alloy, e.g. such as Hastelloy C, as it is each defined hereinafter in more detail.

Thus, without being limited to, for example, in an embodiment of the invention, the microreactor suitable for, preferably for industrial production, an "SiC-microreactor" that comprises or is made of SiC (silicon carbide; e.g. SiC as offered by Dow Corning as Type G1SiC or by Chemtrix MR555 Plantrix), e.g. providing a production capacity of from about 5 up to about 400 kg per hour; or without being limited to, for example, in another embodiment of the invention the microreactor suitable for industrial production comprises or is made of Hastelloy C, as offered by Ehrfeld. Such microreactors are particularly suitable for the, preferably industrial, production of HCFC-123 (2,2-dichloro-1,1,1-trifluoroethane) and/or of HCFC-122 (1,1,2-trichloro-2,2-difluoroethane).

In order to meet both the mechanical and chemical demands placed on production scale flow reactors, Plantrix modules are fabricated from 3M™ SiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 B1 and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10^{-6} K^{-1}$).

Designed for flow rates ranging from 0.2 to 20 ml/min and pressures up to 25 bar, Protrix® allows the user to develop continuous flow processes at the lab-scale, later transitioning to Plantrix® MR555 (×340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarized as follows; possible reaction types are, e.g. A+B→P1+Q (or C)→P, wherein the terms "A", "B" and "C" represent educts, "P" and "P1" represent products, and "Q" represent quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300×250; number of modules/frame is one (minimum) up to four (max.). More technical information on the ChemtrixProtrix® reactor can be found in the brochure "CHEMTRIX—Scalable Flow Chemistry—Technical Information Protrix®, published by Chemtrix BV in 2017, which technical information is incorporated herein by reference in its entirety.

The Dow Corning as Type G1SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type G1SiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively. The reactor configuration of Dow Corning as Type G1SiC microreactor is characterized as multi-purpose and configuration can be customized. Injection points may be added anywhere on the reactor.

Hastelloy® C is an alloy represented by the formula $NiCr_{21}Mo_{14}W$, alternatively also known as "alloy 22" or "Hastelloy® C-22. The alloy is well known as a highly corrosion resistant nickel-chromium-molybdenum-tungsten alloy and has excellent resistance to oxidizing reducing and mixed acids. The alloy is used in flue gas desulphurization plants, in the chemical industry, in environmental protection systems, in waste incineration plants, and in sewage plants. Apart from the above examples, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0.35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur).

In such case of low amounts (i.e. ≤0.1%) of other elements, the elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%. Normally, no traceable amounts of any of the following elements are found in the alloy compositions indicated below: Nb (niobium), Ti (titanium), Al (aluminum), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel); 57% (balance); Co (cobalt) 2.5% (max.); Cr (chromium); 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

In another embodiments of the invention, without being limited to, for example, the microreactor suitable for the production, preferably for the industrial production, is an SiC-microreactor that comprises or is made only of SiC as the construction material (silicon carbide; e.g. SiC as offered by Dow Corning as Type G1SiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of HCFC-123 (2,2-dichloro-1,1,1-trifluoroethane) and/or of HCFC-122 (1,1,2-trichloro-2,2-difluoroethane). If more than one microreactor, preferably more than one SiC-microreactors, are used in the production, preferably in the industrial production, of HCFC-123 (2,2-dichloro-1,1,1-trifluoroethane) and/or of HCFC-122 (1,1,2-trichloro-2,2-difluoroethane), then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory research, e.g. on applicable reaction and/or upscaling conditions, without being limited to, for example, a microreactor, the reactor type Plantrix of the company Chemtrix is suitable.

For example, an industrial flow reactor ("IFR", e.g. Plantrix® MR555) comprises SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises one SiC module (e.g. 3M® SiC), a mixer ("MRX") that affords access to A+B→P type reactions. Increasing the number of modules leads to increased reaction times and/or system productivity. The addition of a quench Q/C module extends reaction types to A+B→P1+Q (or C)→P and a blanking plate gives two temperature zones. Herein the terms "A", "B" and "C" represent educts, "P" and "P1" represent products, and "Q" represent quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MRH" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)<70° C.; reagent feeds of 1 to 3; maximum operating pressure (service fluid) of about 5 bar at a temperature of about 200° C.; maximum operating pressure (process fluid) of about 25 bar at a temperature of about ≤200° C.

The processes of the invention employ a halogenation catalyst, preferably a fluorination catalyst. Halogenation is a chemical reaction that involves the addition of one or more halogens to a compound or material. The pathway and stoichiometry of halogenation depends on the structural features and functional groups of the organic substrate, as well as on the specific halogen. Inorganic compounds such as metals also undergo halogenation. Fluorination is a halogenation wherein F (fluorine) is the halogen introduced into a compound or material. Halogenation and/or fluorination are well known to those skilled in the art, as well as the halogenation catalysts and/or fluorination catalysts involved in these reactions. For example, the addition of halogens, e.g. chlorine and/or fluorine, to alkenes proceeds via intermediate halonium ions as an active species, wherein "halonium ion" in organic chemistry denotes any onium compound (ion) containing a halogen atom, e.g., herein in the context of the invention a fluorine atom carrying a positive charge.

Halogenation catalysts and/or fluorination catalysts are well known to those skilled in the field, and preferably in the context of the invention, based on Sb, As, Bi, Al, Zn, Fe, Mg, Cr, Ru, Sn, Ti, Co, Ni, preferably on the basis of Sb. More preferably a fluorination catalyst, especially an Sb fluorination catalysts providing the active species $H_2F^+SbF^{6-}$.

In a first embodiment (1), the invention relates to a process for the manufacture of HCFC-123 (2,2-dichloro-1,1,1-trifluoroethane) comprising the steps of:

(a) providing HCFC-122 (1,1,2-trichloro-2,2-difluoroethane) as a starting material or intermediate material;

(b) providing HF (hydrogen fluoride) and a catalyst, preferably a halogenation promoting catalyst, more preferably a fluorination promoting catalyst, optionally providing HF (hydrogen fluoride) and a catalyst as a recycling mixture and additionally fresh HF as required (for example by reason of stoichiometry);

(c) mixing the HCFC-122 of (a) with the HF and the catalyst of (b);

(d) feeding the mixture obtained in (c) into at least one continuous flow reactor with upper lateral dimensions of about ≤4 mm, preferably into at least one microreactor, and therein carrying out the reaction of HCFC-122 with HF in the presence of the catalyst to obtain a reaction mixture comprising HCFC-123;

preferably into at least one microreactor under one or more of the following conditions:

flow rate: from about 10 ml/h up to about 400 l/h;
temperature: from about 30° C. up to about 150° C.;
pressure: from about 5 bar up to about 50 bar;
residence time: from about 1 minute up to about 60 minutes;

(e) withdrawing the reaction mixture obtained in (d) from the continuous flow reactor, preferably from the microreactor, to yield a HCFC-123 comprising product, preferably a HCFC-123 product, more preferably a product comprising or consisting essentially of HCFC-123; and (f) optionally purifying and/or isolating the HCFC-123 product obtained in (e) to yield purified and/or isolated HCFC-123.

In a second embodiment (2), the invention relates to a process for the manufacture of HCFC-122 (1,1,2-trichloro-2,2-difluoroethane) comprising the steps of:

(a) providing PER (tetrachloroethylene) and/or pentachloroethane, preferably PER (tetrachloroethylene), as a starting material;

(b) providing HF (hydrogen fluoride) and catalyst, preferably a halogenation promoting catalyst, more preferably a fluorination promoting catalyst;

(c) mixing the PER of (a) with the HF and the catalyst of (b);

(d) feeding the mixture obtained in (c) into at least one continuous flow reactor with upper lateral dimensions of about ≤4 mm, preferably into at least one microreactor, and therein carrying out the reaction of PER with HF in the presence of the catalyst to obtain a reaction mixture comprising HCFC-122;

preferably into at least one microreactor under one or more of the following conditions:

flow rate: from about 10 ml/h up to about 400 l/h;
temperature: from about 30° C. up to about 150° C.;
pressure: from about 5 bar up to about 50 bar;
residence time: from about 1 minute up to about 60 minutes;

(e) withdrawing the reaction mixture obtained in (d) from the continuous flow reactor, preferably from the microreactor, to yield a HCFC-122 comprising product, preferably a HCFC-122 product, more preferably a product comprising or consisting essentially of HCFC-122; and (f) optionally purifying and/or isolating the HCFC-122 product obtained in (e) to yield purified and/or isolated HCFC-122.

In a third embodiment (3), the invention relates to a process for the manufacture of HCFC-123 (2,2-dichloro-1,1,1-trifluoroethane) according to embodiment (1), wherein in the step (a), the HCFC-122 (1,1,2-trichloro-2,2-difluoroethane) provided as a starting material or intermediate material is obtained by a process for the manufacture of HCFC-122 (1,1,2-trichloro-2,2-difluoroethane) as defined in embodiment (2).

In a fourth embodiment (4), the invention relates to the process for the manufacture of HCFC-123 (2,2-dichloro-1,1,1-trifluoroethane) according to embodiment (1), or the process for the manufacture of HCFC-122 (1,1,2-trichloro-2,2-difluoroethane) to embodiment (2), wherein at least one of the continuous flow reactors, preferably at least one of the microreactors, in step (d) independently is a SiC-continuous flow reactor, preferably independently is aSiC-microreactor.

In a fifth embodiment (5), the invention relates to a process for the manufacture of HCFC-123 (2,2-dichloro-1,1,1-trifluoroethane) according to embodiment (4), wherein the at least one of the microreactors in step (d) independently is aSiC-microreactor, preferably wherein the at least one of the microreactors in step (d) is aSiC-microreactor in the step (d) as defined in embodiment (1).

In a sixth embodiment (6), the invention relates to a process according to any one of the embodiments (1) to (5), wherein the catalyst is a halogenation catalyst, preferably a fluorination catalyst, on the basis of Sb, As, Bi, Al, Zn, Fe, Mg, Cr, Ru, Sn, Ti, Co, Ni, preferably on the basis of Sb, more preferably a fluorination catalyst wherein the fluorination catalyst is selected from the group consisting of Sb fluorination catalysts providing the active species $H_2F^+$ $SbF_6^-$.

In a seventh embodiment (7), the invention relates to a process according to embodiment (6), wherein the halogenation catalyst is antimony pentachloride and/or antimony pentafluoride, preferably wherein the catalyst is antimony pentafluoride ($SbF_5$) and is prepared in an autoclave by reaction of $SbCl_5$ with HF, more preferably consisting of $SbF_5$ in HF which forms the active species $H_2F^+SbF_6^-$, prior to reaction step (d) in the process according to any one of embodiments (1) to (3).

In an eighth embodiment (8), the invention relates to a process according to any one of the preceding embodiments (1) to (7), wherein the process comprises step (f) purifying and/or isolating the HCFC-122 product obtained in (e) as defined in embodiment (2) to yield purified and/or isolated HCFC-122, and/or wherein the process comprises step (f) purifying and/or isolating the HCFC-123 product obtained in (e) as defined in embodiment (1) to yield purified and/or isolated HCFC-123.

Preferably, in the process as defined in embodiment (3), the HCFC-122 (1,1,2-trichloro-2,2-difluoroethane) is obtained by a process for the manufacture of HCFC-122 (1,1,2-trichloro-2,2-difluoroethane) as defined in embodiment (2). Next, by purifying and/or isolating the HCFC-122 product obtained in (e) as defined in embodiment (2) to yield purified and/or isolated HCFC-122 as a starting material or intermediate material for the manufacture of HCFC-123 (2,2-dichloro-1,1,1-trifluoroethane) as defined in embodiment (1).

In a ninth embodiment (9), the invention relates to a process according to the embodiment (8), wherein in step (f) as defined in any one of the embodiments (1) or (2), the purifying and/or isolating of HCFC-122 and/or of the HCFC-123 comprises or consists of a phase separation method, preferably wherein either at least or solely the purifying and/or isolating of HCFC-122 as defined in step (f) of embodiment (2) comprises or consists of a phase separation method.

In a tenth embodiment (10), the invention relates to a process according to any one of the preceding embodiments (1) to (9), wherein at least in step (f) as defined in embodiment (2) for the purifying and/or isolating of HCFC-122 does not comprise a distillation to yield purified and/or isolated HCFC-122, preferably when the purified and/or isolated HCFC-122 is provided to be used in a process for the manufacture of HCFC-123 (2,2-dichloro-1,1,1-trifluoroethane) as defined in embodiment (1), and wherein in the step (a) the HCFC-122 (1,1,2-trichloro-2,2-difluoroethane) provided as a starting material or intermediate material is obtained by a process for the manufacture of HCFC-122 (1,1,2-trichloro-2,2-difluoroethane) as defined in the embodiment (2).

Finally, the present invention also pertains to a continuous flow two-step process for the manufacture of HCFC-123 (2,2-dichloro-1,1,1-trifluoroethane), wherein the HCFC-122 (1,1,2-trichloro-2,2-difluoroethane) provided as a starting material or intermediate material is obtained by a first continuous flow process step, and the HCFC-122 (1,1,2-trichloro-2,2-difluoroethane) obtained from the first continuous flow process step is reacted with HF in the presence of the a catalyst, e.g. a halogenation promoting catalyst, preferably a fluorination promoting catalyst, in a second continuous flow process step to obtain a reaction mixture comprising HCFC-123, withdrawing the reaction mixture from the second continuous flow process step to yield a HCFC-123 comprising product, preferably a HCFC-123 product, more preferably a product comprising or consisting essentially of HCFC-123; and optionally purifying and/or isolating the HCFC-123 product obtained to yield purified and/or isolated HCFC-123. Such a continuous flow two-step process for the manufacture of HCFC-123 (2,2-dichloro-1,1,1-trifluoroethane) according to the invention preferably comprises a purification and/or separation step, wherein the HCFC-122 (1,1,2-trichloro-2,2-difluoroethane) obtained by the first continuous flow process step, prior to its use as a starting material or intermediate material for the manufacture of HCFC-123 (2,2-dichloro-1,1,1-trifluoroethane) in the second continuous flow process step, is subjected to purifying and/or separating to yield a purified and/or separated HCFC-122 product as a starting material or intermediate material for the second continuous flow process step. More preferably the purification and/or separation step to yield purified and/or separated HCFC-122 is a phase separation method.

Accordingly, in one embodiment, the invention pertains to a continuous flow two-step process for the manufacture of HCFC-123 (2,2-dichloro-1,1,1-trifluoroethane) comprising the steps of:
 (i) providing HCFC-122 (1,1,2-trichloro-2,2-difluoroethane) as a starting material or intermediate material by a first continuous flow two-step process comprising the steps of:
   (a) providing PER (tetrachloroethylene) and/or pentachloroethane, preferably PER (tetrachloroethylene), as a starting material;
   (b) providing HF (hydrogen fluoride) and catalyst, preferably a halogenation promoting catalyst, more preferably a fluorination promoting catalyst;

(c) mixing the PER of (a) with the HF and the catalyst of (b);

(d) feeding the mixture obtained in (c) into at least one first continuous flow reactor, and therein carrying out the reaction of PER with HF in the presence of the catalyst to obtain a reaction mixture comprising HCFC-122;

most preferably into at least one first microreactor under one or more of the following conditions:
flow rate: from about 10 ml/h up to about 400 l/h;
temperature: from about 30° C. up to about 150° C.;
pressure: from about 5 bar up to about 50 bar;
residence time: from about 1 minute up to about 60 minutes;

(e) withdrawing the reaction mixture obtained in (d) from the first continuous flow reactor, most preferably from the first microreactor, to yield a HCFC-122 comprising product, preferably a HCFC-122 product, more preferably a product comprising or consisting essentially of HCFC-122; and (ii) optionally purifying and/or separating the HCFC-122 product obtained in (e) to yield purified and/or separated HCFC-122, preferably, wherein the purification and/or separation step to yield purified and/or separated HCFC-122 is a phase separation method;

(iii) providing HF (hydrogen fluoride) and a catalyst, preferably a halogenation promoting catalyst, more preferably a fluorination promoting catalyst, optionally providing HF (hydrogen fluoride) and a catalyst as a recycling mixture and additionally fresh HF as required (for example by reason of stoichiometry);

(iv) mixing the HCFC-122 of step (i), optionally mixing the HCFC-122 of step (ii), with the HF and the catalyst of (iii);

(v) feeding the mixture obtained in (iv) into at least one second continuous flow reactor, most preferably into at least one microreactor, and therein carrying out the reaction of HCFC-122 with HF in the presence of the catalyst to obtain a reaction mixture comprising HCFC-123;

preferably into at least one second microreactor under one or more of the following conditions:
flow rate: from about 10 ml/h up to about 400 l/h;
temperature: from about 30° C. up to about 150° C.;
pressure: from about 5 bar up to about 50 bar;
residence time: from about 1 minute up to about 60 minutes;

(vi) withdrawing the reaction mixture obtained in (v) from the second continuous flow reactor, most preferably from the second microreactor, to yield a HCFC-123 comprising product, preferably a HCFC-123 product, more preferably a product comprising or consisting essentially of HCFC-123; and (vii) optionally purifying and/or isolating the HCFC-123 product obtained in (vi) to yield purified and/or isolated HCFC-123.

In the preferred continuous flow two-step process for the manufacture of HCFC-123 (2,2-dichloro-1,1,1-trifluoroethane), independently the continuous flow reactor in the first and/or second continuous flow process step may be independently be selected from the group consisting of a plug flow reactor, a tubular flow reactor, a continuous flow reactor, wherein the chemical reactions take place in a confinement with upper lateral dimensions of about ≤4 mm, a continuous flow reactor, wherein the chemical reactions take place in a confinement with lateral dimensions of from about ≥1 mm up to about ≤4 mm, and a microreactor. Further preferred is a continuous flow two-step process for the manufacture of HCFC-123 (2,2-dichloro-1,1,1-trifluoroethane), wherein independently the continuous flow reactor in the first and/or second continuous flow process step is independently be selected from the group consisting of a continuous flow reactor, wherein the chemical reactions take place in a confinement with upper lateral dimensions of about ≤4 mm, more preferably a continuous flow reactor, wherein the chemical reactions take place in a confinement with lateral dimensions of from about ≥1 mm up to about ≤4 mm, and most preferably a microreactor.

The invention, employing at least one microreactor, preferably employing at least one SiCmicroreactor, provides the advantages in that the processes for the manufacture of HCFC-123 (2,2-dichloro-1,1,1-trifluoroethane) and/or of HCFC-122 (1,1,2-trichloro-2,2-difluoroethane) are industrially feasible, e.g. easily scalable to industrial yields of HCFC-123 and/or optionally of HCFC-122, and in that the process in particular shows improved (e.g. good) selectivity and low energy consumption for the targeted products of HCFC-123 and/or optionally of HCFC-122. Especially, it is an advantage of the presentinvention in that it provides an improved and/or optimized process for the manufacture of HCFC-123, in particular by reacting HCFC-122 as a starting material or intermediate material with HF in the presence of the catalyst. A particular advantage is also that the present-invention provides an improved and/or optimized process for the manufacture of HCFC-123 and/or for the manufacture of HCFC-122, wherein the HCFC-123 and/or the HCFC-122 can be easily, e.g., by a method with only low energy consumption, purified and/or isolated, and wherein preferably the process for purifying and/or isolating does not require a distillation. Advantageously, especially in comparison to a distillation method used in the prior arts, the separation, in particular of HCFC-122 (density=1.55 g/cm$^3$), but if desired also of HCFC-123, from excess HF (density=0.99 g/cm$^3$) and from the catalyst can easily take place in an energy-saving manner by phase separation. Furthermore, the processes for the manufacture of HCFC-123 (2,2-dichloro-1,1,1-trifluoroethane) and/or of HCFC-122 (1,1,2-trichloro-2,2-difluoroethane) can be efficiently combined in that HCFC-122 (1,1,2-trichloro-2,2-difluoroethane) produced by the method according the invention by using a microreactor, preferably aSiCmicroreactor, may preferably advantageously serve as a starting material and/or intermediate material in the manufacture of HCFC-123 (2,2-dichloro-1,1,1-trifluoroethane), preferably also in a microreactor.

Thus, a particular advantage of the method of the invention is a high conversion and/or high selectivity, and especially both, high conversion and high selectivity.

In FIG. 1, an exemplary embodiment of a process scheme for the manufacture of HCFC-123 (2,2-dichloro-1,1,1-trifluoroethane) and/or of HCFC-122 (1,1,2-trichloro-2,2-difluoroethane) is shown. Herein, the HCFC-122 (1,1,2-trichloro-2,2-difluoroethane) produced from tetrachlorethylene in the presence of a catalyst (antimony pentafluoride, SbF$_5$) in a first microreactor can be purified and/or isolated to yield HCFC-122 (1,1,2-trichloro-2,2-difluoroethane) as the final product; and/or the HCFC-122 (1,1,2-trichloro-2,2-difluoroethane) produced in a first microreactor, optionally can be purified, and then be used as starting material and/or intermediate material in the manufacture of HCFC-123 (2,2-dichloro-1,1,1-trifluoroethane) in a second microreactor, again in the presence of HF and a catalyst (antimony pentafluoride, SbF$_5$); also it is shown that additional fresh HF is introduced into the second microreactor, for reason of stoichiometry. The catalyst antimony pentafluoride (SbF$_5$) can be used as such, e.g. prepared prior to reaction in an autoclave by reaction of SbCl$_5$ with HF, consists of SbF$_5$ in HF which forms the active species H$_2$F$^+$SbF$^{6-}$, or may be formed in situ by reacting antimony pentachloride (SbCl$_5$) with HF. Herein, more than one microreactor, preferably more than one SiC-microreactors, are used in the production, preferably in the industrial production, of HCFC-123 (2,2-dichloro-1,1,1-trifluoroethane) and/or of HCFC-122 (1,1,2-trichloro-2,2-difluoroethane), and these microreactors, preferably these SiC-microreactors, are used in a subsequent arrangement. For example, here two microreactors are used in a sequence, preferably here two SiC-microreactors are used in a sequence, in the production, preferably in the industrial production, of HCFC-123 (2,2-dichloro-1,1,1-trifluoroethane) and/or of HCFC-122 (1,1,2-trichloro-2,2-difluoroethane).

Although, FIG. 1 exemplifies the use of two microreactors, of course as described above, the first and/or second reactor independently can be a microreactor in combination with a continuous flow reactor with upper lateral dimensions of about ≤4 mm as defined above, or can also be continuous flow reactor with upper lateral dimensions of about ≤4 mm as defined above, without employing a microreactor, e.g. independently a plug flow reactor with upper lateral dimensions of about ≤4 mm and/or tubular flow reactor with upper lateral dimensions of about ≤4 mm.

In the FIG. 1, the term "cat" means "catalyst" especially a halogenation catalyst, more particularly a fluorination catalyst; the term "PCE" means "PER" or tetrachloroethylene or perchlorethylene (Cl$_2$C═CCl$_2$).

In this exemplary embodiment of FIG. 1, the first microreactor suitable for industrial production is, e.g., made of SiC as offered by Dow Corning as Type G1SiC or Chemtrix MR555 Plantrix (5 to 400 kg per hour) or, e.g. of Hastelloy C as offered by Ehrfeld. For the second microreactor, the construction material is SiC only. It is of course possible to use SiC-microreactors twice, e.g. as a first SiC-microreactor for the manufacture of HCFC-122 (1,1,2-trichloro-2,2-difluoroethane), and then subsequently e.g. as a second SiC-microreactor for the manufacture of HCFC-123 (2,2-dichloro-1,1,1-trifluoroethane) from HCFC-122 (1,1,2-trichloro-2,2-difluoroethane) obtained in the first SiC-microreactor. For laboratory search, e.g. on applicable reaction and/or upscaling conditions, for example, as a microreactor the reactor type Plantrix of the company Chemtrix is also suitable as a first and/or as a second microreactor.

Furthermore, in this exemplary embodiment of FIG. 1, the separation of HCFC-122 from excess HF (density=0.99 g/cm$^3$) and from the catalyst is easily performed in an energy-saving manner by phase separation (density=1.55 g/cm$^3$).

In addition to the preferred embodiments of the present invention using PER (tetrachloroethylene) as a starting material in a process for the manufacture of HCFC-122 (1,1,2-trichloro-2,2-difluoroethane) according to the invention, in addition or alternatively to PER (tetrachloroethylene), it is also possible to provide in step (a) pentachloroethane as a starting material in the process of manufacturing HCFC-122.

Accordingly, the invention also relates to a process for the manufacture of HCFC-122 (1,1,2-trichloro-2,2-difluoroethane) comprising the steps of:

(a) providing PER (tetrachloroethylene) and/or pentachloroethane preferably PER (tetrachloroethylene), as a starting material;

(b) providing HF (hydrogen fluoride) and a catalyst, preferably a halogenation promoting catalyst, more preferably a fluorination promoting catalyst;

(c) mixing the PER of (a) with the HF and the catalyst of (b);

(d) feeding the mixture obtained in (c) into at least one microreactor and therein carrying out the reaction of PER with HF in the presence of the catalyst to obtain a reaction mixture comprising HCFC-122;
preferably under one or more of the following conditions:
flow rate: from about 10 ml/h up to about 400 l/h;
temperature: from about 30° C. up to about 150° C.;
pressure: from about 5 bar up to about 50 bar;
residence time: from about 1 minute up to about 60 minutes;

(e) withdrawing the reaction mixture obtained in (d) from the microreactor to yield a HCFC-122 comprising product, preferably a HCFC-122 product, more preferably a product comprising or consisting essentially of HCFC-122; and (f) optionally purifying and/or isolating the HCFC-122 product obtained in (e) to yield purified and/or isolated HCFC-122.

The possibly allegeable disadvantage of this variant using pentachloroethane as the educt (starting material) is the reaction of the formation of two moles of HCl, whereas the use of PER only one mole of HCl is formed. However, this disadvantage may also be seen only as subjective point of view, but on the other hand under certain process constraints in a region or at a production facility may still be appropriate, and formation of additional HCl may be considered of less importance or even being desired.

The industrial application of HCFC-123 is once as a raw material for HCFC-125 and as a raw material for trifluoroacetyl chloride (TFAC) which in turn is an intermediate for a variety of agrochemicals and pharmaceuticals. In terms of industrial application, the HCFC-122 is once the starting material for the preparation of HCFC-123, for example as described herein also according to the invention, but after being produced in a microreactor. If necessary or desired, the HCFC-122 can also be isolated as a product itself from phase separator. Or the HCFC-122 can also be used as a starting material for the manufacture of chlorodifluoroacetyl chloride, which is also an intermediate for agrochemicals and pharmaceuticals.

The following examples are intended to further illustrate the invention without limiting its scope.

Example: Manufacture of HCFC-122 (1,1,2-Trichloro-2,2-Difluoroethane) and of HCFC-123 (2,2-Dichloro-1,1,1-Trifluoroethane)

Reference is made to the process scheme shown in FIG. 1.

The first microreactor used is a SiC-microreactor Module Protrix (Chemtrix) with a volume of 20 ml, while the second microreactor consists of 4 modules with a total volume of 80 ml to increase the residence time. The catalyst, prepared prior to reaction in an autoclave by reaction of SbCl$_5$ with HF, consists of SbF$_5$ in HF (optionally with some traces of HCl) which forms the active species H$_2$F$^+$SbF$^{6-}$. The concentration of Sb in the HF is set at 10 mol %. The pressure in the first reactor 1 (pressure maintenance valve on the cyclone) is set to 10 bar, the temperature is set to 80° C. HF and PER (tetrachloroethylene) are pumped from storage tanks each with a pump in an upstream mixer and then in the first microreactor in the amount so that a residence time of 5 minutes is reached (ratio HF/PER=4:1). The storage tank with HF also contains the previously prepared catalyst $SbF_5$. The HCl/HF mixture escaping from the cyclone (contains mainly HCl) is separated in a downstream HCl pressure column into commercializable HCl and HF, where the HF is fed back into the reaction. The first phase separator has a volume of 500 ml to allow the reaction mixture sufficient time for separation. The HF/catalyst phase is pumped back into the HF circuit into the HF tank and mixed with fresh HF corresponding to the HF consumption. In the next step, the obtained phase containing mainly HCFC-122 is pumped from the first phase separator into a second SiC-microreactor 2 (temperature 100° C.) and is mixed with the HF-mixture, comprising the catalyst, from the HF tank (ratio HF/HCFC-122=8:1). The pressure maintenance of the second stage takes place again on the cyclone and is set to 15 bar. Note: Since the catalyst mixture can be deactivated during the reaction in the first microreactor 1 and the second microreactor 2 by (low) conversion of Sb(V) to Sb(III) reaction, after the phase separators, as required, either $F_2$ or $Cl_2$ is fed into the catalyst stream, for regenerating the Sb(III) to the more active Sb(V). The HF catalyst phase of the second phase separator is also fed back into the HF tank, and the phase which is now mainly containing HCFC-123 (with possibly only traces HCFC-123a) is subjected to a fine distillation under atmospheric pressure in a steel column to yield pure HCFC-123. The isolated yield of pure HCFC-123 is 97%.

What is claimed is:

1. A process of manufacturing $CHCl_2CF_3$ (HCFC-123), comprising:
    (a) providing $CHCl_2CClF_2$ (HCFC-122);
    (b) providing HF and a catalyst;
    (c) mixing the HCFC-122 in the step (a) with the HF and the catalyst in the step (b);
    (d) feeding the mixture obtained in the step (c) into at least one continuous flow reactor with upper lateral dimensions of about ≤4 mm, and carrying out the reaction of the HCFC-122 with the HF in the presence of the catalyst in the at least one continuous flow reactor to obtain a reaction mixture comprising $CHCl_2CF_3$ (HCFC-123); and
    (e) taking out the reaction mixture obtained in the step (d) from the continuous flow reactor to yield a product comprising HCFC-123.

2. The process of claim 1, wherein the HCFC-122 in the step (a) is formed by reacting tetrachloroethylene (PER) with HF and the catalyst.

3. The process of claim 1, wherein the continuous flow reactor is a microreactor under at least one of the following conditions:
    flow rate: from about 10 ml/h up to about 400 l/h;
    temperature: from about 30° C. up to about 150° C.;
    pressure: from about 5 bar up to about 50 bar; and
    residence time: from about 1 minute up to about 60 minutes.

4. The process of claim 3, wherein the microreactor is a SiC microreactor.

5. The process of claim 1, wherein the catalyst is a halogenation catalyst based on Sb, As, Bi, Al, Zn, Fe, Mg, Cr, Ru, Sn, Ti, Co, Ni, or any combinations thereof.

6. The process of claim 5, wherein the halogenation catalyst is a fluorination catalyst.

7. The process of claim 6, wherein the fluorination catalyst is based on Sb.

8. The process of claim 7, wherein the fluorination catalyst provides an active species $H_2F^+SbF_6^-$ formed by $SbF_5$ in HF before the step (d).

9. The process of claim 1, further comprising:
    (f) purifying the HCFC-123 product obtained in the step (e) to yield purified HCFC-123.

10. The process of claim 9, wherein the step (f) comprises a phase separation method.

11. A process of manufacturing $CHCl_2CClF_2$ (HCFC-122), comprising:
    (a) providing tetrachloroethylene (PER);
    (b) providing HF and a catalyst;
    (c) mixing the PER in the step (a) with the HF and the catalyst in the step (b);
    (d) feeding the mixture obtained in the step (c) into at least one continuous flow reactor with upper lateral dimensions of about ≤4 mm, and carrying out the reaction of the HCFC-122 with the HF in the presence of the catalyst in the at least one continuous flow reactor to obtain a reaction mixture comprising $CHCl_2CClF_2$ (HCFC-122); and
    (e) taking out the reaction mixture obtained in the step (d) from the continuous flow reactor to yield a product comprising HCFC-122.

12. The process of claim 11, wherein the continuous flow reactor is a microreactor under at least one of the following conditions:
    flow rate: from about 10 ml/h up to about 400 l/h;
    temperature: from about 30° C. up to about 150° C.;
    pressure: from about 5 bar up to about 50 bar; and
    residence time: from about 1 minute up to about 60 minutes.

13. The process of claim 12, wherein the microreactor is a SiC microreactor.

14. The process of claim 11, wherein the catalyst is a halogenation catalyst based on Sb, As, Bi, Al, Zn, Fe, Mg, Cr, Ru, Sn, Ti, Co, Ni, or any combinations thereof.

15. The process of claim 14, wherein the halogenation catalyst is a fluorination catalyst.

16. The process of claim 15, wherein the fluorination catalyst is based on Sb.

17. The process of claim 16, wherein the fluorination catalyst provides an active species $H_2F^+SbF_6^-$ formed by $SbF_5$ in HF before the step (d).

18. The process of claim 11, further comprising:
    (f) purifying the HCFC-122 product obtained in the step (e) to yield purified HCFC-122.

19. The process of claim 18, wherein the step (f) comprises a phase separation method.

* * * * *